United States Patent [19]

Saksena et al.

[11] Patent Number: 5,015,739

[45] Date of Patent: * May 14, 1991

[54] PROCESSES FOR PREPARATION OF CYCLOPENTYL PURINE DERIVATIVES

[75] Inventors: Anil K. Saksena, Upper Montclair; Viyyoor M. Girijavallabhan, Parsippany; Ashit K. Ganguly, Upper Montclair, all of N.J.

[73] Assignee: Schering Corporation, Kenilworth, N.J.

[*] Notice: The portion of the term of this patent subsequent to Mar. 12, 2008 has been disclaimed.

[21] Appl. No.: 185,176

[22] Filed: Apr. 22, 1988

[51] Int. Cl.$^5$ .................. C07D 473/34; C07D 473/18; C07D 473/30; C07D 473/04

[52] U.S. Cl. .................................. 544/277; 544/265; 544/267; 544/268; 544/276

[58] Field of Search ............... 544/277, 276, 265, 267, 544/268

[56] References Cited

U.S. PATENT DOCUMENTS

| | | | |
|---|---|---|---|
| 4,172,829 | 10/1979 | Naito et al. | 544/277 X |
| 4,232,155 | 11/1980 | Naito et al. | 544/277 |
| 4,782,062 | 11/1988 | Tolman et al. | 514/262 |
| 4,803,272 | 2/1989 | Anton et al. | 544/277 |
| 4,916,224 | 4/1990 | Vince et al. | 544/254 |
| 4,931,559 | 6/1990 | Vince et al. | 544/276 |

FOREIGN PATENT DOCUMENTS

| | | |
|---|---|---|
| 0219838 | 4/1987 | European Pat. Off. . |
| 0236935 | 9/1987 | European Pat. Off. . |
| 0267878 | 5/1988 | European Pat. Off. . |
| 0291229 | 11/1988 | European Pat. Off. . |

OTHER PUBLICATIONS

Vince et al., Antiviral Research, vol. 9 (1/2), 120 (1/2/88).

Vince et al., Biochemical and Biophysical Research Communications, vol. 156, No. 2, pp. 1046-1053 (10/31/88).

Trost et al., J. Am. Chem. Soc., vol. 110, No. 2, pp. 621-622 (01/20/88).

Zorbach et al., editors, *Synthetic Procedures in Nucleic Acid Chemistry*, vol. 1, Copyright 1968 by John Wiley & Sons, Inc., pp. 202-204.

Howard J. Schaeffer, D. D. Godse, & Georgiana Liu, Enzyme Inhibitors III, Syntheses of cis-(6-Substituted-9-Purinyl)Cycloalkylcarbinols as Adenosine Inhibitors, Journal of Pharmaceutical Sciences, vol. 53, No. 12, Dec. 1964, pp. 1510-1515.

Victor E. Marquez & Mu-Ill Lim, Carbocyclic Nucleosides, Medicinal Research Reviews, vol. 6, No. 1, 1-40 (1986).

*Primary Examiner*—Diana Rivers
*Attorney, Agent, or Firm*—Joseph T. Majka; Henry C. Jeanette

[57] ABSTRACT

Cyclopentyl purine derivatives, novel intermediate thereof and processes for their preparation are disclosed.

13 Claims, No Drawings

PROCESSES FOR PREPARATION OF CYCLOPENTYL PURINE DERIVATIVES

FIELD OF THE INVENTION

The present invention is directed to novel intermediates useful in preparing cyclopentyl purine derivatives. The present invention is also directed to a novel process for preparing the cyclopentyl purine derivatives and their intermediates.

BACKGROUND OF THE INVENTION

Cyclopentyl purine derivatives are compounds useful in gene cloning and are known to possess antiviral activity against DNA viruses or RNA viruses. European Patent Application 236935 teaches certain cyclopentyl derivatives as having antiviral activity against DNA viruses such as DNA viruses, herpes virus group (e.g. herpes simplex virus type I or II, cytomegalovirus, Epstein-Barr virus), Hepatitis B virus; or RNA viruses such as human immunodeficiency virus (HIV) which is a pathogen of acquired immunodeficiency syndrome (AIDS), vesicular stomatitis virus, feline leukemia virus and equine infectious anemic virus.

European Patent Application 219838 discloses analogues of cyclopentyl purine derivatives.

A review paper by Victor E. Marquez and Mu-Ill Lim (1986) Medicinal Research Reviews, Vol. 6, No. 1, pages 1–40 by John Wiley & Sims, Inc. teaches numerous cyclopentyl derivatives as well as methods for their preparation.

Although functional, the processes taught for preparing the cyclopentyl purine derivatives of European Patent Application 236935 have the disadvantage of requiring numerous reaction steps. Further, in some of the reaction steps, intermediates must be individually purified before further reaction, requiring even further steps for preparation. Also, in numerous processes protecting groups must be utilized in order to carry out the process. It would be desirable to employ a process for preparing cyclopentyl purine derivatives which requires as few or even fewer steps than other processes previously taught It would also be desirable to employ a process which can utilize intermediates which can be readily used for further reaction with little or no purification. It would also be desirable to provide intermediates which can be used in such a process. Further, it would be desirable to employ a process which does not require the use of protecting groups in order to carry out the process.

SUMMARY OF THE INVENTION

The present invention discloses a process for preparing a 6'-hydroxy cyclopentyl derivative of the formula:

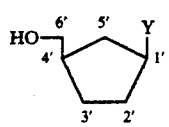

(X)

wherein Y is purine or modified purine which is adenin-9-yl, hypoxanthin-9-yl, guanin-9-yl, or xanthin-9-yl and bound via the nitrogen atom at the 9-position in the purine or the modified purine.

The process comprises the steps of:

(a) contacting at least one 2',3'-dihydroxy cyclopentyl derivative of the formula:

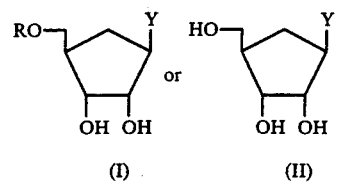

wherein
Y is as defined hereinbefore,
R is alkyl, alkenylalkyl, alkynylalkyl, alkoxyalkyl, dialkylaminoalkyl, alkylthioalkyl, benzyl, alkylbenzyl, alkoxybenzyl, phenyl, alkoxyphenyl, alkylphenyl, cycloalkyl, cycloalkalkyl, or —COR$^7$,
wherein
R$^7$ is alkyl, benzyl, alkylbenzyl, alkoxybenzyl, phenyl, alkylphenyl, cycloalkyl or cycloalkalkyl,
with a compound of the formula:

wherein
R$^2$ and R$^3$ independently represent C-1 to C-3 alkyl;
Z represents
—OR$^1$ wherein R$^1$ represents the same values as for R$^2$ or R$^3$, or
—NR$^4$R$^5$ wherein R$^4$ and R$^5$ independently represent hydrogen or the same values for R,
in the presence of an acid catalyst to yield at least one 2',3'-cyclic ortho ester of the formula:

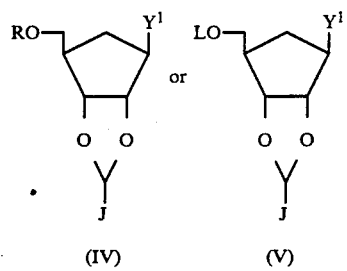

wherein
R is as defined hereinbefore,
J represents —OR$^1$, —OR$^2$, —OR$^3$ or —NR$^4$R$^5$, and
L represents hydrogen, —CHOR$^1$OR$^2$, —CHOR$^1$OR$^3$, —CHOR$^2$OR$^3$, —CHOR$^1$NR$^4$R$^5$, —CHOR$^2$NR$^4$R$^5$, —CHOR$^3$NR$^4$R$^5$ or —CHO,
Y$^1$ is the same as Y with the proviso that any free amino function (i.e. —NH$_2$) present in Y can be the Schiff base, —N=CHZ, or —NHCHOR$^2$NR$^4$R$^5$, —NHCHOR$^3$NR$^4$R$^5$, or —NHCHOR$^2$OR$^3$
wherein Z, R$^1$, R$^2$, R$^3$, R$^4$ and R$^5$ are as defined hereinbefore;

(b) contacting at least one 2', 3'-cyclic ortho ester from step (a) with an anhydride under substantially anhydrous conditions to yield at least one 2', 3'-dehydro derivative of the formula:

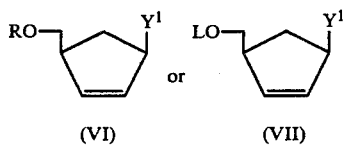 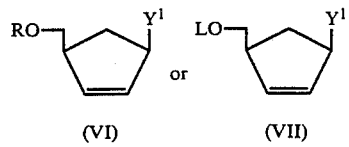

(c) for those derivatives of $Y^1$ having the Schiff base —N=CHZ, hydrolyzing the Schiff base to reform the free amino function;

(d) contacting at least one 2', 3'-dehydro derivative from step (b) or (c) with a hydrogenating agent to yield at least one cylcopentyl analogue of the formula:

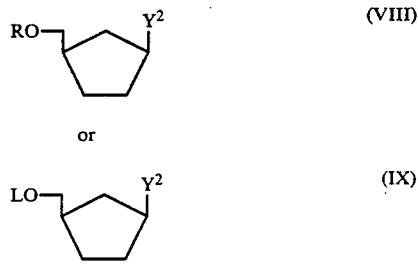

wherein R and L are as defined hereinbefore and
$Y^2$ is the same as Y with the proviso that the amino function is free or —NHCHOR$^2$NR$^4$R$^5$, —NHCHOR$^3$NR$^4$R$^5$ or —NHCHOR$^2$OR$^3$;

(e) hydrolyzing at least one cyclopentyl analogue from step (d) to the 6'-hydroxy cyclopentyl derivative of formula (X).

Optionally and preferably, the process further comprises step (f), recovering said 6'-hydroxy cyclopentyl derivative of formula (X) from the reaction mixture.

As to the 2', 3'-dihydroxy cyclopentyl derivative of formula (II), preferably Y is adenin-9-yl. As to the compound (III), preferably Z is OR$^1$, and R$^1$, R$^2$ and R$^3$ are methyl.

In another embodiment of the present invention, any 6'-hydroxy cyclopentyl derivative of formula (X) is recovered from the reaction mixture following the hydrogenation in step (d) of the above process.

In yet another embodiment of the present invention are provided 2', 3'-cyclic ortho esters of the formula:

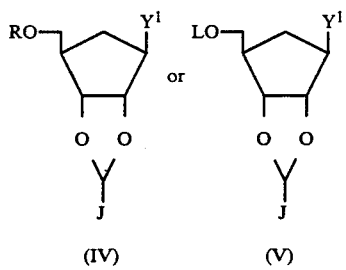

wherein $Y^1$, R, J and L are as defined hereinbefore. Preferably $Y^1$ is adenine or adenine whose amino function is —NHCHOR$^2$OR$^3$ and L is hydrogen, —CHOR$^1$OR$^2$, —CHOR$^1$OR$^3$ or —CHOR$^2$OR$^3$; and J is —OR$^1$, —OR$^2$ or —OR$^3$. Most preferably, $Y^1$ is adenin-9-yl or adenin-9-yl whose amino function is —NHCH(OCH$_3$)$_2$; L is hydrogen or —CH(OCH$_3$)$_2$ and J is —OCH$_3$.

In yet another embodiment, the present invention is directed to 2', 3'-dehydro derivatives of the formula:

wherein
R, $Y^1$ and L are as defined hereinbefore.
Preferably L is hydrogen or —CHOR$^1$OR$^2$, —CHOR$^1$OR$^3$ or —CHOR$^2$OR$^3$ and $Y^1$ is adenin-9-yl or adenin-9-yl whose amino function is —NHCHOR$^2$OR$^3$. Most preferably, L is hydrogen or —CH(OCH$_3$)$_2$ and Y is adenin-9-yl or adenin-9-yl whose amino function is —NHCH(OCH$_3$)$_2$.

The present invention has the advantage of providing a process for preparing cyclopentyl purine derivatives in which fewer steps are required than with other processes previously taught The process of the present invention also has the advantage of utilizing intermediates which can be readily used for further reaction with little or no purification. The present invention also has the further advantage of not utilizing protective groups in order to carry out the process The intermediate compounds of the present invention are believed to possess anti-viral properties.

DETAILED DESCRIPTION OF THE INVENTION

The term "alkyl" is used in the present specification and in the appended claims to designate a straight or branched saturated hydrocarbon moiety (i.e. hydrocarbons having carbon-carbon single bonds) containing from 1 to 6 carbon atom, such as for example, methyl, ethyl, propyl, isopropyl, butyl, isobutyl, tertbutyl, pentyl, hexyl and the like.

The term "alkoxy" refers to an alkoxy moiety containing from 1 to 6 carbon atoms, such as for example, methoxy, ethoxy, propoxy, isopropoxy, butoxy, pentoxy and the like.

The term "alkenyl" refers to a straight or branched hydrocarbon moiety of two to six carbon atoms having one carbon-carbon double bond.

The terms "halogen" and "halo" refers to fluoride, chloride, bromide or iodide.

The term "alkynyl" refers to a straight or branched hydrocarbon chain of two to six carbon atoms having one carbon to carbon triple bond such as propargyl.

The term "alkenylalkyl" refers to an alkenyl moiety of two to six carbon atoms covalently bonded to a alkyl moiety of 1 to 6 carbon atoms.

The term "alkynylalkyl" refers to an alkynyl moiety of two to six carbon atoms covalently bonded to an alkyl moiety of 1 to 6 carbon atoms The term "alkoxyalkyl" refers to an alkoxy moiety of 1 to 6 carbon atoms covalently bonded to an alkyl moiety of 1 to 6 carbon atoms.

The term "dialkylaminoalkyl" refers to a tertiary amino group having 1 to 6 carbon atoms in each alkyl moiety.

The term "alkylthioalkyl" refers to an alkyl moiety of 1 to 6 carbons covalently bonded to another alkyl moiety of 1 to 6 carbon atoms through a thio moiety.

The term "alkylbenzyl" refers to a phenylmethyl moiety having alkyl moiety of one to six carbon atoms on the phenyl ring.

The term "alkoxybenzyl" refers to a phenylmethyl moiety having an alkoxy moiety of one to six carbon atoms on the phenyl ring.

The term "alkoxyphenyl" refers to a phenyl moiety having an alkoxy group of one to six carbon atoms on the phenyl ring.

The term "alkylphenyl" refers to a phenyl moiety having an alkyl moiety of one to six carbon atoms on the phenyl ring.

The term "cycloalkyl" refers to a saturated carbocyclic ring characterized by closed rings and containing from 3 to 6 carbon atoms, such as for example, cyclopropyl, cyclobutyl, cyclopentyl, cyclohexyl, and the like.

The term "cycloalkalkyl" refers to a cycloalkyl moiety of 3 to 6 carbon atoms covalently bonded to an alkyl moiety of 1 to 6 carbon atoms.

In step (a) of the process, at least one 2', 3'-dihydroxy cyclopentyl derivative of formula (I) or (II) can be contacted with compound (III) in the presence of an acid catalyst in amounts and under conditions effective to yield the 2', 3'-cyclic ortho ester of formula (IV) or (V). Generally and preferably, the reactants can be contacted under substantially anhydrous conditions, such as those provided by the use of dry reagents and reaction vessels. In addition, anhydrous conditions can be provided by a blanket of an inert gas, such as nitrogen, argon, helium or mixtures thereof The compound (III) wherein Z is $-OR^1$ is generally known as an ortho ester When $R^1$, $R^2$ and $R^3$ are methyl, compound (III) is methyl orthoformate, known as trimethoxymethane. In another embodiment of compound (III), Z can be $-NR^4R^5$ as defined hereinbefore, as exemplified by N,N-dimethyl formamide dimethyl acetal Employment of compounds wherein Z is $-NR^4R^5$ or $-OR^1$ can yield a Schiff base at any free amino moiety (i.e. $-NH^2$) in the purine, such as adenin-9-yl or guanin-9-yl.

The contacting of the reactants can be performed neat, although co-solvents also can be employed along with the compound (III) in order to solubilize the reactants. Suitably compatible solvents include but are not limited to N,N-dimethyl formamide (DMF), N,N-dimethyl acetamide (DMA), dioxane, dimethyl sulfoxide (DMSO), and mixtures thereof. The amount of co-solvent to compound (III) can range from about 10 to 1:1, preferably from about 5 to 1:1 (parts by weight co-solvent:part compound (III)).

Compound (III) can be contacted with the 2', 3'-dihydroxy cyclopentyl derivative of formula (I) or (II) in amounts ranging from about 100 to 1:1, preferably from about 25 to 10:1 (moles compound (III):mole 2', 3'-dihydroxy cyclopentyl derivative (I) or (II)). Compound (III) can also serve as a solvent in the process, when employed in excess amounts to solubilize the 2', 3'-dihydroxy cyclopentyl derivative (I) or (II). The contacting of the reactants can be carried at temperature ranging from about ambient to about 100 degrees Centigrade (° C.), preferably from about ambient to about 50° C. The contacting can be normally carried out at ambient pressures with stirring or other means of agitation.

The acid catalyst can be a mineral acid such as hydrochloric acid (HCl), sulfuric acid ($H_2SO_4$), phosphoric acid ($H_3PO_4$), mixtures thereof and the like. The acid catalyst can also be an organic acid such as o, m-, or p-toluene sulfonic acid, acetic acid, benzoic acid, trichloroacetic acid, trifluoroacetic acid, mixtures thereof, and the like. The acid catalyst can be employed in catalytically effective amounts. For example, amounts from about 0.1 to about 2 mole percent, based on reactants are suitable, preferably amounts of from about 1 to about 1.5 mole percent If desired, the 2', 3'-cyclic ortho ester of formula (IV) or (V) thus prepared can be recovered by conventional recovery procedures, such as phase separation, distillation or evaporation of any solvents present, crystallization, chromatography, filtration and the like. Alternatively, the reaction mixture containing the 2', 3'-cyclic ortho ester is directly employed in step (b).

In step (b), at least one 2', 3'-cyclic ortho ester (IV) or (V) from step (a) is contacted with an anhydride in amounts and under conditions effective to yield at least one 2', 3'-dehydro derivatives of formula (VI) or (VII).

Representative anhydrides having from 4 to 10 carbon atoms include, but are not limited to acetic anhydride, benzoic propionic anhydride, n-butyric anhydride, acetic benzoic anhydride, heptanoic anhydride, and sulfonic acid anhydrides such as trifluoromethane sulfonic anhydride, or mixtures thereof, most preferably acetic anhydride.

Generally, the reactants are contacted under substantially anhydrous conditions such as described hereinbefore. The anhydride can be contacted with the 2', 3'-cyclic ortho esters (IV) or (V) in amounts ranging from about 50 to 1:1, preferably from about 26 to 10:1 (moles anhydride:mole 2', 3' cyclic ortho ester (IV or V)). The contacting of the reactants is carried out at temperatures ranging from about 100° C. to reflux, preferably from about 100 to 150° C. The pressures and stirring requirements are similar to those described for step (a). Where sulfonic acid anhydrides are employed, moreover, somewhat milder reaction conditions can be utilized. For example, the contacting can be performed at temperatures ranging between about 20 to about 75° C. for about 30 minutes or more. The contacting can be performed in the presence of a secondary amine compound such as diisopropyl amine in a solvent such as toluene See, for example, N.C. Yank et al., Tetrahedran Letters, 3919-3922 (1987); S. Hanessian et al., Tetrahedran Letters, 737-740 (1978); F.W. Eastwood et al., Tetrahedran Letters, 5223-5224 (1970).

If desired, the 2', 3'-dehydro derivatives of formula (VI) or (VII) can be recovered from the reaction mixture of step (b) by conventional recovery procedures such as those described hereinbefore. Alternatively, the reaction mixture containing the 2', 3'-dehydro derivatives are employed directly in step (c).

During step (b) the Schiff base $-N=CHZ$ can be formed at the free amino function (i.e. $-NH_2$ moiety) in the purine or modified purine moiety (i.e. Y) where in compound (III), Z is $-NR^4R^5$, or $-OR^1$ is employed. For any Schiff base formed, the Schiff base can be hydrolyzed to re-form the free amino moiety as described in step (c). Generally, excess anhydride is removed by separating procedures described herein before (i.e. evaporation in vacuo) and the Schiff base can be hydrolyzed to the free amino function with an acid or base. For example, the reaction mixture can be contacted with a base such as aqueous pyridine containing ammonium hydroxide in amounts and under conditions effective to hydrolyze the Schiff's base to give the free amino function. Step (c) may be unnecessary where only small or negligible amounts of the Schiff base are formed in the purine or modified purine (i.e. Y). Following reformation of the free amino function the reaction mixture can be subsequently treated as described in step (d).

In step (d), at least one 2', 3'-dehydro derivative (VI or VII) is contacted with a hydrogenating agent in amounts and under conditions effective to yield at least one cyclopentyl analogue of a derivative of formula (VIII) or (IX). The term "hydrogenating agent" is intended to include the requisite hydrogenating catalyst(s) and hydrogen ($H_2$) source for hydrogenating the 2', 3'-dehydro derivatives (VI or VII). Various selected catalysts and conditions are described in "Catalytic Hydrogenation in Organic Synthesis", (1978) Morris Freifelder, Chapter 4, Olefins, pages 15-25, John Wiley and Sons. The hydrogenating catalyst can be nickel, palladium, platinum, platinum oxide, platinum on carbon, and mixtures thereof. Preferably the hydrogenating catalyst is palladium on carbon. The source of hydrogen can be hydrogen gas ($H_2$) or isotopic forms thereof, such as deuterium or tritium.

The hydrogenating catalyst is employed in catalytic amounts effective to convert the 2', 3'-dehydro derivative (VI or VII) to the cyclopentyl analogues (VIII) or (IX). Such amounts preferably can range from 30 to 0.1:1, more preferably from about 5 to 1:1 (moles hydrogenating catalyst:mole 2', 3'-dehydro derivatives (VI or VII)). Equimolar amounts of hydrogen to the cyclopentyl analogues (VIII or IX) can be employed, although excess amounts of hydrogen can be used. The temperature for contacting during hydrogenation can range from about ambient to about 50° C., preferably ambient. The contacting of the 2', 3'-dehydro derivatives (VI) or (VII) with the hydrogenating agent generally can be carried out at ambient pressures or at pressures greater than ambient in a Parr-type reactor with stirring or other means of agitation. The contacting can be carried out in the presence of a solvent, such as a C-1 to C-8 alcohol such as methanol, ethanol and the like; or in ethyl acetate or acetic acid. The solvent can be employed in amounts ranging from about 100-10 parts by weight solvent to one part reactant Following completion of the reaction in step (d), the hydrogenating catalyst can be separated from the reaction mixture by conventional separating procedures such as filtration, centrifugation, decantation and the like. Any 6'-hydroxy cyclopentyl derivative (X) thus present can be recovered by conventional procedures such as described hereinbefore. Alternatively and preferably as a matter of convenience, any 6'-hydroxy cyclopentyl derivative (X) present in the reaction mixture is treated together with any cyclopentyl analogues (VIII or IX) during hydrolysis in step (e).

In step (e) at least one cyclopentyl analogue (VIII) or (IX) is hydrolyzed to the desired 6'-hydroxy cyclopentyl derivative (X). The hydrolysis preferably is carried out by adding to the reaction medium a mineral or organic acid as described hereinbefore, preferably hydrochloric acid, followed by heating the reaction media to a temperature ranging from ambient to about 50° C., preferably ambient temperatures, under ambient pressures with stirring or other means for agitation. The acid is employed in amounts effective to hydrolyze the cyclopentyl analogues (VIII or IX), preferably from about 25 to about 1 molar equivalent acid to 1 molar equivalent cyclopentyl analogue (VIII or IX), preferably about 15 molar equivalents acid can be employed Alternatively, the cyclopentyl analogues (VIII or IX) can be saponified with slight excess molar amount of alkali such as sodium carbonate ($Na_2CO_3$) or potassium carbonate ($K_2CO_3$); and heated under a dry inert atmosphere such as nitrogen or helium at temperatures ranging from about ambient to about 100° C. After cooling, the reaction mixture can be acidified with an acid such as those described hereinbefore.

In step (f), the desired 6'-hydroxy cyclopentyl derivative (X) can be recovered by conventional procedures described hereinbefore. For example, after acidification the reaction media can be extracted with a suitable water immiscible solvent such as diethyl ether, ethyl acetate, chloroform, n-butanol and the like. The organic phase can be washed with brine, dried over a drying agent such as magnesium sulfate ($MgSO_4$) and concentrated to dryness.

The following examples illustrate the present invention in a manner by which it can be practiced, but as such, should not be construed as limitations upon the overall scope of the same. In the examples which follow, the wavy line (∼) of the 2', 3'-cyclic ortho ester is intended to represent either of the two stereo-isomeric forms of the 2', 3'-cyclic ortho esters:

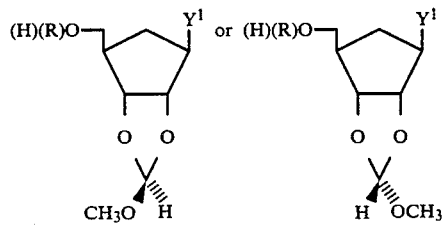

Step (a): Preparation of 2', 3'-Cyclic Ortho Esters

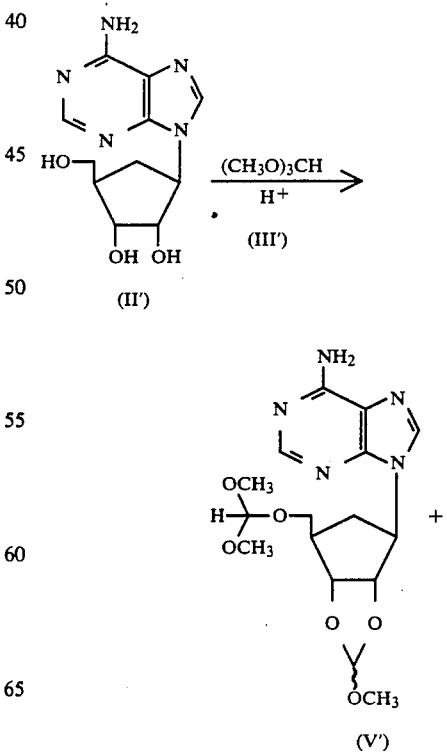

-continued

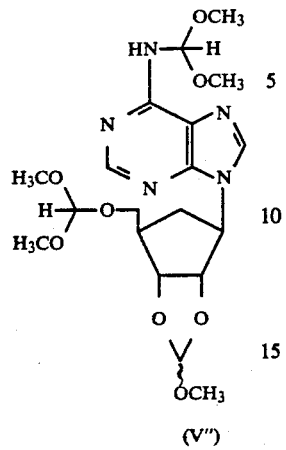

(V''')

Aristeromycin 10 grams (g) is stirred with 100 milliliters (ml) methyl orthoformate ((CH₃O)₃CH) and dry dimethylformamide (30 ml) in the presence of p-toluenesulfonic acid monohydrate (10.3 g). After about 36 hours stirring at room temperature, 15 g anhydrous potassium carbonate (K₂CO₃) is added and the mixture is stirred for about 2 hours. The solids containing potassium tosylate are removed by filtration and washed with minimum amounts of methyl orthoformate and toluene. The combined filtrates and washings are evaporated in-vacuo in a bath having a temperature of 40° to 50° C. to provide a gummy residue. The gummy residue is azeotroped with 100 ml toluene on a rotary evaporator to remove the methyl orthoformate, and gives a mixture of title 2', 3'-cyclic ortho esters (V') and (V''), together with a small amount of unidentified compounds.

Proton magnetic resonance spectroscopy (PMR) (CDCl₃): δ1.8(m), 2.47(m), 2.88(s), 2.95(s), 3.27(s), 3.29(s), 3.35(s), 3.42(s), 3.44(s), 3.74(m), 3.9(m), 4.8(m), 5.09(d), 5.15(m), 5.62(broad s), 5.65(m), 5.88(d), 5.94(s), 7.84(s), 7.85(s), 7.86(s), 8.32(s), 8.33(s). These compounds are used in step (b) infra.

Step (b): Preparation of 2', 3'-Dehydro derivatives

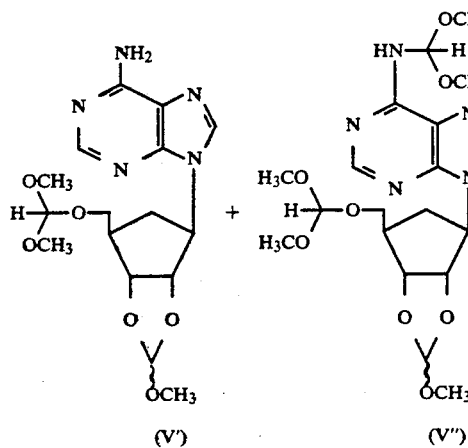

(V')  (V'')

↓ (CH₃CO)₂O

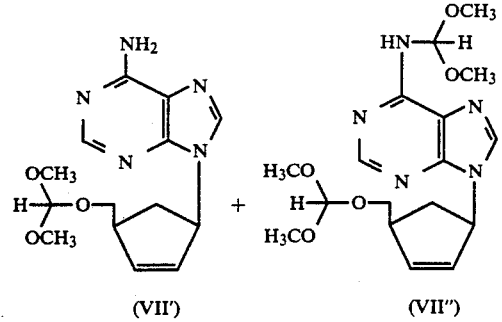

(VII')  (VII'')

The mixture from step (a) is first refluxed overnight with 100 ml acetic anhydride ((CH₃CO)₂O) under argon atmosphere. After heating overnight, the dark reaction mixture is evaporated in-vacuo and the dark brown gummy product remaining is filtered through a column of silica (SiO₂) (300 g). The column is prepared in 2 percent methanol/methylene chloride. After a 500 ml forerun, the eluting fractions of 300 ml per fractions are collected. Fractions two through eight are combined to give the 2', 3'-dehydro derivatives (VII' and VII''), together with a small amount of unidentified compounds. PMR (CDCl₃): δ1.7(m), 1.85(s), 1.97(s), 2.01(s), 2.28(s), 2.54(s), 2.9(m), 3.18(m), 4.1(m), 5.0(m), 5.75–5.8(m), 5.8(m), 5.9(m), 6.17(m), 8.09(s), 8.1(s), 8.16(s), 8.67(s), 8.89(s), 9.4–9.5(m).

These compounds are used in the step (d) without further purification.

Step (d): Preparation of Cyclopentyl Purine Derivatives

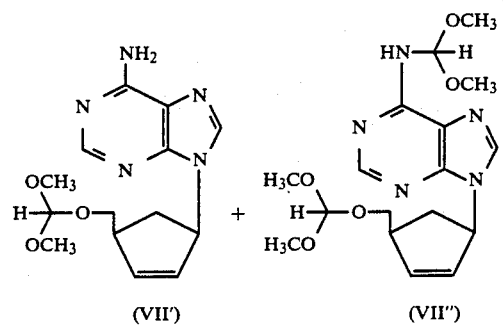

(VII')  (VII'')

↓ Pd/C / H₂

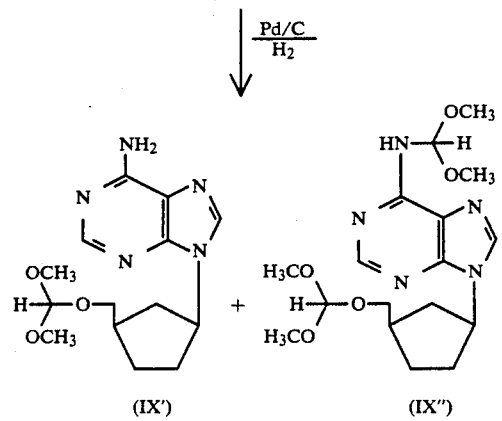

(IX')  (IX'')

The 2', 3'-dehydro derivatives (VII' and VII'') obtained in step (c) are dissolved in ethanol and hydrogenated with 5 percent Palladium/carbon (Pd/C) (0.15 g)

in a Paar hydrogenator until no starting material could be detected by thin-layer chromatography. The catalyst is removed by filtration, the reaction mixture is washed with ethanol and the combined filtrate and washings are evaporated to dryness in vacuo to give 9.18 of the cyclopentyl purine derivatives (IX' and IX"), together with a small amount of unidentified compounds.

Step (e): Preparation of 6'-Hydroxy cyclopentyl derivative (2', 3'-deoxyaristeromycin)

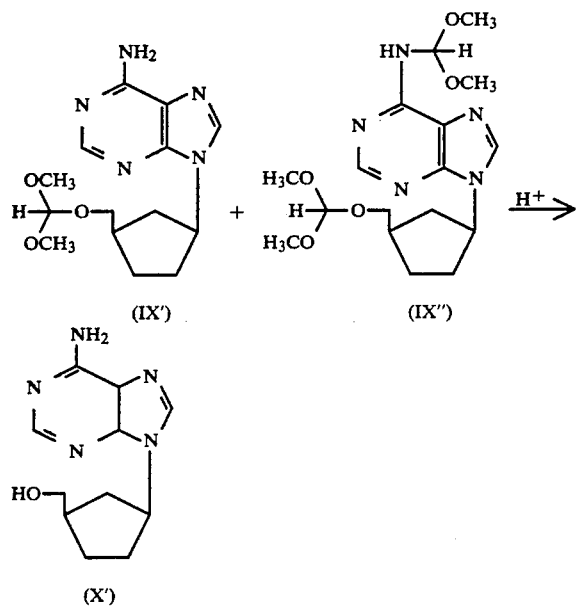

The cyclopentyl purine derivatives from step (c) are dissolved in 6 Normal (N) HCl (120 ml) and let to stand overnight at room temperature. A small amount of gummy precipitate present is removed by filtration. The aqueous acidic solution is concentrated to dryness in-vacuo, and the residue is taken up in 60 ml concentrated NH4OH (28 percent). After four hours the aqueous solution is concentrated and the residue remaining is chromatographed on silica gel (160 g). The column is eluted with 5 to 8 percent methanol/methylene chloride and 150 ml fractions are collected. Fractions containing the desired 6'-hydroxy cyclopentyl derivative, as determined by thin layer chromatography, are combined to provide 4.08 g of 2', 3'-deoxyaristeromycin (X'), a solid. A small portion of the solid is recrystallized from ethyl acetate to give rod-shaped crystals, melting point 127–128° C.

PMR (DMSO-d6): 1.65(m), 1.75(m), 2.05(m), 2.15(m), 2.25(m), 2.5 (broad s), 3.42(m), 4.57(t), 4.8(m), 7.12(s), 8.1(s), 8.2(s).

Mass Spec.: FAB [M+H]+234

$[\alpha]^{26}_D$ —6.3°(9.83 mg/2ml H2O)

Analysis: $C_{11}H_{15}ON_5$ (Molecular weight: 233).

Calculated—C:56.63, H:6.48, N:30.02.

Found - C:56.60, H:6.48, N:30.68.

The structure of 2', 3'-Deoxyaristeromycin is further confirmed by X-ray analysis.

Preparation of Starting Materials

The 2', 3'-dihydroxy cyclopentyl derivatives of formulas (I) and (II) used in preparing the desired 6'-hydroxy cyclopentyl derivative of formula (X) are either known or can be prepared by the methods described in European Patent Applications 219838 and 236935 and in review paper by Marquiz and Mu-Ill Lim, cited hereinbefore. The 2', 3'-dihydroxy cyclopentyl derivative of formula (II), wherein Y is adenosine, is known as aristeromycin (3-(6-amino-9H-purin-9-yl)-5-(hydroxymethyl)-1,2-cyclopentanediol), Stereoisomeric form -1R-(1α, α, 3β, 5β). Methods for preparing aristeromycin are described in U.S. Pat. No. 4,594,350; in Japanese Patent, JP 60/215685 A2 29 October 1985; in JP 57/94288 A2 11 June 1982; in JP 52/128395 27 October 1977; in JP 50/62992 29 May 1975; in JP 45/23596 7 August 1970; and in various articles such as (CA107(19):176398c) "A new route to (−)-aristeromycin and (−)-neplanocin A via the asymmetric Diels-Alder cycloaddition", Arai, Yoshitsusu; Hayashi, Yoshikazu; Yamamoto, Masatoshi; Takayama, Hiromitsu; Koizum; Toru Fac. Pharm. Sci., Toyama Med. Pharm. Univ. Toyama 930-01, Japan Chem. Letter, (1), 185–6;

(CA105(25):224496r)—Creation of novel chiral synthons with pig liver esterase application to natural product synthesis and the substrate recognition. Ohno, Masaji; Kobayashi, Susumu; Adachi, Kunitomo Fac. Pharm. Sci., Univ. Tokyo, Tokyo 113, Japan. NATO ASI Ser., Ser. C. 178 (Enzymes Catal. Org. Synth.), 123-42 16-2 (Fermentation and Bioindustrial Chemistry);

(CA103(19):160794k) - Resolution of aristeromycin enantiomers, Herdewijn, Piet; Balzarini, Jan; De Clerca; Erik; Vanderhaeshe, Hubert, Resa Inst. Med. Res., Kathol. Univ. Leuven Louvain B-3000, Belg., J. Med. Chem. 28(10). 1385-6;

(CA79(15):87815x) - Analogs of S-adenosylhomocysteine as potential inhibitors of biological transmethylation. Specificity of the S-adenosylhomocysteine binding site. Coward, James K.; Slisz, Edwin P.. Sch. Med., Yale University, New Haven, Conn., USA. J. Med. Chem., 16(5), 460-3; and (CA104(19):168742h) - A novel and stereospecific synthesis of (+)− and (−)-aristeromycin. Madhavan, G.V. Bindu; Martin, John C.. Syntex Res., Palo Alto, CA 94304, USA. J. Org. Chem., 51(8), 1287-93.

The preparative teachings of these references for aristeromycin are incorporated herein by reference.

The compound (III) wherein Z is —OR[1] is generally known as a tertiary orthoester. These compounds can be prepared from orthoformic acid, otherwise known as methanetriol or trihydroxymethane. Generally, the hydrogens of the hydroxyl groups are replaced by selected C-1 to C-3 alkyl groups, giving rise to orthoformic esters, as described in W.H. Post, The Chemistry of the Aliphatic Orthoesters (Reinhold, N.Y., 1943) 188 pp.; Chu, Shen C.A. 38,2930 (1944) and in Sah, Ma, J. Am. Chem. Soc. 54, 2965 (1932), in Robert H. DeWolfe, Synthesis of Carboxylic and Carbonic Ortho Esters (1974) Synthesis, pp. 153–156, in Ando et al, A Mild and Stereospecific Conversion of Vicinal Diols into Olefins Via 2-Methoxy-1,3-Dioxolane Derivatives, (1986) Chemistry Letters, pp 879–882, and in von Hans Meerwein et al, Über Säureamidacetale, Harnstoffacetaleund Lactamacetale, (1961), Liebigs Ann. Chem. Bd. 641, pp. 2.

The compounds (III) wherein Z is —NR[4]R[5] can be prepared in accordance with known procedures, such as those described in H. Meerwein, W. Florian, N. Schön and G. Stopp, Ann., 641.1 (1961), in F.W. Eastwood et al, The Conversion of 2-Dimethylamino-1,3-Dioxolans into Alkenes, (1970) Tetrahedron Letters No. 60, pp. 5223–5224, and in John L. King, Stereospecific Deoxygenation of 1,2-diols to Olefins, (1987) Tetrahedron Letters, Vol. 28, No. 34, pp. 3919–3922.

While the present invention has been described in conjunction with the specific embodiments set forth above, many alternatives, modifications, and variations thereof will be appoint to those of ordinary skill in the art. All such alternatives, modifications and variations are intended to fall within the spirit and scope of the present invention.

What is claimed is:

1. Method for preparing a 6'-hydroxycyclopentyl derivative of the formula:

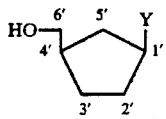
(X)

wherein Y is purine or modified purine which is adenin-9-yl, hypoxanthin-9-yl, guanin-9-yl, and xanthin-9-yl and bound via the nitrogen atom at the 9-position in the purine or the modified purine comprising:

(a) contacting at least one 2', 3'-dihydroxy cyclopentyl derivative of the formula:

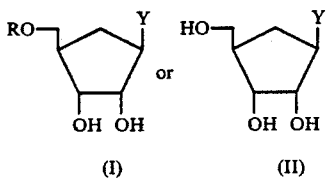
(I)    (II)

wherein
Y is as defined hereinbefore,
R is alkyl of 1 to 6 carbon atoms, alkenylaklyl of 1 to 6 carbon atoms in the alkyl moiety, alkynlalkyl of 1 to 6 carbon atoms in the alkyl moiety, alkoxyalkyl of 1 to 6 carbon atoms in the alkyl moiety, dialkylaminoalkyl of 1 to 6 carbon atoms in each alkyl moiety, alkylthioalkyl of 1 to 6 carbon atoms in each alkyl moiety, benzyl, alkylbenzyl of 1 to 6 carbon atoms in the alkyl moiety, alkoxybenzyl of 1 to 6 carbon atoms in the alkoxy group, phenyl, alkoxyphenyl of 1 to 6 carbon atoms in the alkyl moiety, alkylphenyl of 1 to 6 carbon atoms in the alkyl moiety, cycloalkyl of 3 to 6 carbon atoms, cycloalkalkyl of 3 to 6 carbon atoms in the cycloalkyl moiety and 1 to 6 carbon atoms in the alkyl moiety, or —COR$^7$, wherein
R$^7$ is alkyl of 1 to 6 carbon atoms, benzyl, alkylbenzyl of 1 to 6 carbon atoms in the alkyl moiety, alkylbenzyl of 1 to 6 carbon atoms in the alkoxy group, phenyl, alkylphenyl of 1 to 6 carbon atoms in the alkyl moiety, cycloalkyl of 3 to 6 carbon atoms or cycloalkalkyl of 3 to 6 carbon atoms in the cycloalkyl moiety and 1 to 6 carbon atoms in the alkyl moiety, with a compound of the formula:

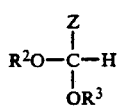
(III)

wherein $R^2$ and $R^3$ independently are C-1 to C-3 alkyl;
Z is
—OR$^1$ wherein R$^1$ is the same value as for R$^2$ or R$^3$, or
—NR$^4$R$^5$ wherein R$^4$ and R$^5$ independently are hydrogen or the same values for R, in the presence of an acid catalyst to yield at least one 2', 3'-cyclic ortho ester of the formula:

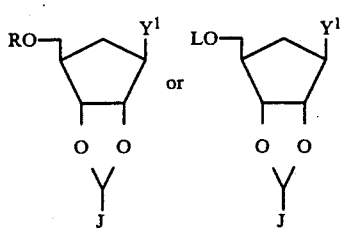
(IV)    (V)

wherein R is as defined hereinbefore,
J is —OR$^1$ or —NR$^4$R$^5$, and
L is hydrogen, —CHOR$^1$OR$^2$, —CHOR$^1$OR$^3$, —CHOR$^2$OR$^3$, —CHOR$^1$NR$^4$R$^5$, —CHOR$^2$NR$^4$R$^5$, —CHOR$^3$NR$^4$R$^5$ or —CHO, and
Y$^1$ is the same as Y with the proviso that any amino function present in Y can be free or can be converted to the Schiff base, —N=CHZ, —NHCHOR$^2$NR$^4$R$^5$, —NCHOR$^3$NR$^4$R$^5$, or —NHCHOR$^2$OR$^3$,
wherein Z, R$^1$, R$^2$, R$^3$, R$^4$ and R$^5$ are as defined hereinbefore;

(b) contacting at least one 2', 3'-cyclic ortho ester from step (a) with an anhydride under substantially anhydrous conditions to yield at least one 2', 3'-dehydro derivative of the formula:

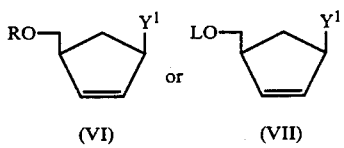
(VI)    (VII)

(c) for those derivatives of Y$^1$ having the Schiff base —N=CHZ, hydrolyzing the Schiff base to reform the free amino function;

(d) contacting at least one 2', 3'-dehydro derivative from step (b) or (c) with a hydrogenating agent to yield at least one cyclopentyl analogue of the formula:

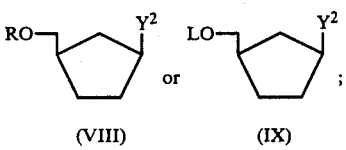
(VIII)    (IX)

wherein R and L are as defined hereinbefore; and
Y$^2$ is the same as Y with the proviso that the amino function is free or —NHCHOR$^2$NR$^4$R$^5$, —NHCHOR$^3$NR$^4$R$^5$, or —NHCHOR$^2$OR$^3$;

(e) hydrolyzing at least one cyclopentyl analogue from step (d) to the 6'-hydroxy cyclopentyl derivative of formula (X).

2. The process of claim 1 further comprising step (f), recovering said 6'-hydroxy cyclopentyl derivative of formula (X) from the reaction mixture.

3. The process of claim 1, where in step (a), as to the 2', 3'-dihydroxy cyclopentyl derivative of formula (II), Y is adenine, and in compound (III), Z is —$OR^1$ and $R^1$, $R^2$ and $R^3$ are methyl 4. The process of claim 1 wherein step (a) is conducted in the presence of a co-solvent.

5. The process of claim 4 where in step (a) the co-solvent is dimethyl formamide.

6. The process of claim 1 where in step (a) the acid catalyst is toluenesulfonic acid.

7. The process of claim 1 where in step (a), the reactants are contacted under substantially anhydrous conditions.

8. The process of claim 1 wherein step (b) the anhydride is acetic anhydride.

9. The process of claim 1 where in step (b) the anhydrous conditions are provided, in part by contacting the reactants under a blanket of an inert gas, which is nitrogen, helium, argon or mixtures thereof.

10. The process of claim 1 wherein in step (d) the hydrogenating agent is palladium on carbon together with a hydrogen source.

11. The process of claim 1 wherein in step (e) the cyclopentyl analogue is hydrolyzed with an acid.

12. The process of claim 11, wherein the acid is hydrochloric acid.

13. The process of claim 1 wherein any 6'-hydroxy cyclopentyl derivative of formula (X) present in the reaction mixture is recovered after hydrogenation in step (d) and before hydrolysis in step (e).

* * * * *